US007996260B1

(12) United States Patent
Cunningham et al.

(10) Patent No.: US 7,996,260 B1
(45) Date of Patent: Aug. 9, 2011

(54) PROMOTIONAL CARRIER FOR PROMOTING PHARMACEUTICAL PRESCRIPTION PRODUCTS

(75) Inventors: David W. Cunningham, Raleigh, NC (US); Brandon Tyndell, Raleigh, NC (US)

(73) Assignee: Trialcard, Inc., Raleigh, NC (US)

( * ) Notice: Subject to any disclaimer, the term of this patent is extended or adjusted under 35 U.S.C. 154(b) by 2143 days.

(21) Appl. No.: 10/833,366

(22) Filed: Apr. 28, 2004

Related U.S. Application Data

(60) Continuation-in-part of application No. 10/243,214, filed on Sep. 13, 2002, which is a continuation-in-part of application No. 10/098,700, filed on Mar. 15, 2002, which is a continuation-in-part of application No. 09/558,260, filed on Apr. 25, 2000, now Pat. No. 6,859,780, which is a continuation-in-part of application No. 09/137,095, filed on Aug. 20, 1998, now Pat. No. 6,055,507, which is a division of application No. 08/556,466, filed on Nov. 13, 1995, now Pat. No. 5,832,449.

(51) Int. Cl.
*G06Q 30/00* (2006.01)
(52) U.S. Cl. .................................................. 705/14.1
(58) Field of Classification Search ............... 705/14, 705/14.1; 283/16
See application file for complete search history.

(56) References Cited

U.S. PATENT DOCUMENTS

| | | | |
|---|---|---|---|
| 3,845,278 A | 10/1974 | Rex, Jr. | |
| 4,195,864 A * | 4/1980 | Morton et al. | 283/56 |
| 4,695,954 A | 9/1987 | Rose et al. | |
| 4,778,153 A * | 10/1988 | Bachman et al. | 283/101 |
| 4,827,112 A | 5/1989 | Yoshino et al. | |
| 4,857,716 A | 8/1989 | Gombrich et al. | |
| 4,893,270 A | 1/1990 | Beck et al. | |
| 4,908,761 A * | 3/1990 | Tai | 705/14 |
| 4,971,362 A | 11/1990 | Lapsker | |
| 5,048,870 A * | 9/1991 | Mangini et al. | 283/81 |
| 5,181,743 A | 1/1993 | Lloyd | |
| 5,192,854 A * | 3/1993 | Counts | 235/375 |
| 5,542,420 A | 8/1996 | Goldman et al. | |
| 5,612,870 A | 3/1997 | Welner | |
| 5,628,530 A | 5/1997 | Thornton | |
| 5,671,282 A | 9/1997 | Wolff et al. | |

(Continued)

FOREIGN PATENT DOCUMENTS

DE 4311941 A1 11/1994

(Continued)

*Primary Examiner* — John G. Weiss
*Assistant Examiner* — Darnell Pouncil
(74) *Attorney, Agent, or Firm* — Coats & Bennett, P.L.L.C.

(57) ABSTRACT

A prescription pharmaceutical promotional carrier is provided that is effective to promote a series of prescription drugs. The carrier includes first and second portions with the second portion being referred to as a payment vehicle and the first portion being utilized to identify the series of prescription drugs being promoted. In use, a preferred embodiment provides a series of stickers secured to the first portion of the carrier. Each sticker identifies or represents a prescription pharmaceutical product. A doctor may possess one or more of the carriers and may prescribe a prescription drug being promoted by the carrier. If so, the doctor can transfer a sticker identifying the prescription drug to the payment vehicle and separate the payment vehicle from the carrier. The separated payment vehicle is then given to the patient along with a prescription for the identified prescription drug and the patient presents the payment vehicle to a pharmacy where at least a portion of the costs of the prescription drug is paid by a party that sponsored the carrier.

15 Claims, 5 Drawing Sheets

U.S. PATENT DOCUMENTS

| | | | |
|---|---|---|---|
| 5,682,027 A | 10/1997 | Bertina et al. | |
| 5,710,886 A | 1/1998 | Christensen et al. | |
| 5,737,539 A | 4/1998 | Edelson et al. | |
| 5,799,981 A * | 9/1998 | Tung et al. | 283/56 |
| 5,803,498 A * | 9/1998 | Tung et al. | 283/56 |
| 5,822,544 A | 10/1998 | Chaco et al. | |
| 5,867,821 A | 2/1999 | Ballantyne et al. | |
| 6,041,309 A * | 3/2000 | Laor | 705/14.26 |
| 6,292,785 B1 * | 9/2001 | McEvoy et al. | 705/14.36 |
| 6,314,406 B1 * | 11/2001 | O'Hagan et al. | 705/14.23 |
| 2003/0036923 A1 * | 2/2003 | Waldon et al. | 705/2 |

FOREIGN PATENT DOCUMENTS

| | | |
|---|---|---|
| EP | 0354260 A1 | 8/1988 |

* cited by examiner

PROMOTIONAL CARRIER FOR PROMOTING PHARMACEUTICAL PRESCRIPTION PRODUCTS

CROSS REFERENCE TO RELATED TO APPLICATIONS

This is a continuation-in-part of U.S. patent application Ser. No. 10/243,214 filed Sep. 13, 2002, which was a continuation-in-part of U.S. patent application Ser. No. 10/098,700 filed Mar. 15, 2002, which was a continuation-in-part of U.S. patent application Ser. No. 09/558,260 filed Apr. 25, 2000 now U.S. Pat. No. 6,859,780, which was a continuation-in-part of U.S. patent application Ser. No. 09/137,095 filed 20 Aug. 1998, now U.S. Pat. No. 6,055,507, which was a divisional application of U.S. patent application Ser. No. 08/556,466 filed 13 Nov. 1995 now U.S. Pat. No. 5,832,449. The disclosures of these applications and patents are hereby expressly incorporated by reference.

FIELD OF THE INVENTION

The present invention relates to pharmaceutical prescription products and more particularly to a carrier for advertising and promoting pharmaceutical prescription products.

BACKGROUND OF THE INVENTION

In the pharmaceutical industry, the primary method for product promotion of ethical products is the use of outside sales representatives. Company sales representatives target specific physicians and detail the features and benefits of particular pharmaceutical products. Pharmaceutical manufacturers have documented that the most effective method of product promotion involves providing pharmaceutical product samples to prescribers of the products who then pass along the product samples to patients. Physicians therefore receive numerous quantities of pharmaceutical product samples for purposes of conducting patient trials. These trials enable physicians to determine the effectiveness of certain drugs in certain patients for certain diseases, as well as to determine patients' tolerance of the drugs and their compliance with drug administration directions.

Drug manufacturers are continually looking for new and better ways to advertise and promote their prescription drugs. As discussed above, providing sample or trial pharmaceutical products to doctors who in turn give them to patients constitutes one important way that pharmaceutical entities are presently promoting their pharmaceutical products to both doctors and patients. However comprehensive and accurate data that might indicate the effectiveness of such sample or trial programs is difficult to achieve because of a lack of substantial record keeping involving the sample or trial products. Further, in many cases, the doctor will give a patient enough sample or trial products to complete the entire treatment. For a certain promotion budget this obviously limits the exposure of the pharmaceutical sample being promoted.

Although product samples are an extremely effective promotional tool, the manufacturing of drug product samples in addition to normally packaged drug products has proven to be increasingly costly. Pharmaceutical product samples are typically elaborately and expensively packaged and are extremely bulky compared to normally packaged drug products. Pharmaceutical manufacturers must utilize separate product sample packaging lines to specially package drug product samples. Distribution of product samples requires delivery via separate carriers and distribution routes. In addition, drug product samples are typically warehoused separately from normally packaged drug products.

Therefore, there has been and continues to be a need for an efficient and cost effective method for promoting pharmaceutical prescription products.

SUMMARY OF THE INVENTION

The present invention relates to a promotional carrier for promoting prescription pharmaceutical products. The carrier includes at least one payment vehicle separable from the carrier and having a unique identifier that is present in a remote database. The carrier further includes a series of prescription product identifiers where each product identifier identifies a particular prescription product being promoted by the carrier. Further, the identified prescription products on the carrier are associated with the unique identifier of the payment vehicle in the database such that the database reflects the prescription products associated with the payment vehicle. The payment vehicle is adapted to assume an active state which enables the payment vehicle to be used to pay for at least a portion of the cost of one or more prescription products identified on the carrier having the payment vehicle associated therewith.

In addition, the present invention entails a method of promoting one or more prescription pharmaceutical products. This method includes identifying one or more prescription pharmaceutical products on a promotional carrier. The method further includes providing at least one payment vehicle that forms a part of the carrier. The payment vehicle includes a unique identifier that is stored in a remote database. For each promotional carrier the method entails linking in the database the payment vehicle identifier with the identified prescription products of the carrier such that the database reflects which prescription products are associated with each payment vehicle. The payment vehicle may assume an active state which enables a payment vehicle to be used to pay for at least a portion of the cost of at least one of the prescription products identified on the carrier.

Other objects and advantages of the present invention will become apparent and obvious from a study of the following description and the accompanying drawings which are merely illustrative of such invention.

DETAILED DESCRIPTION OF THE INVENTION

Figure 1:
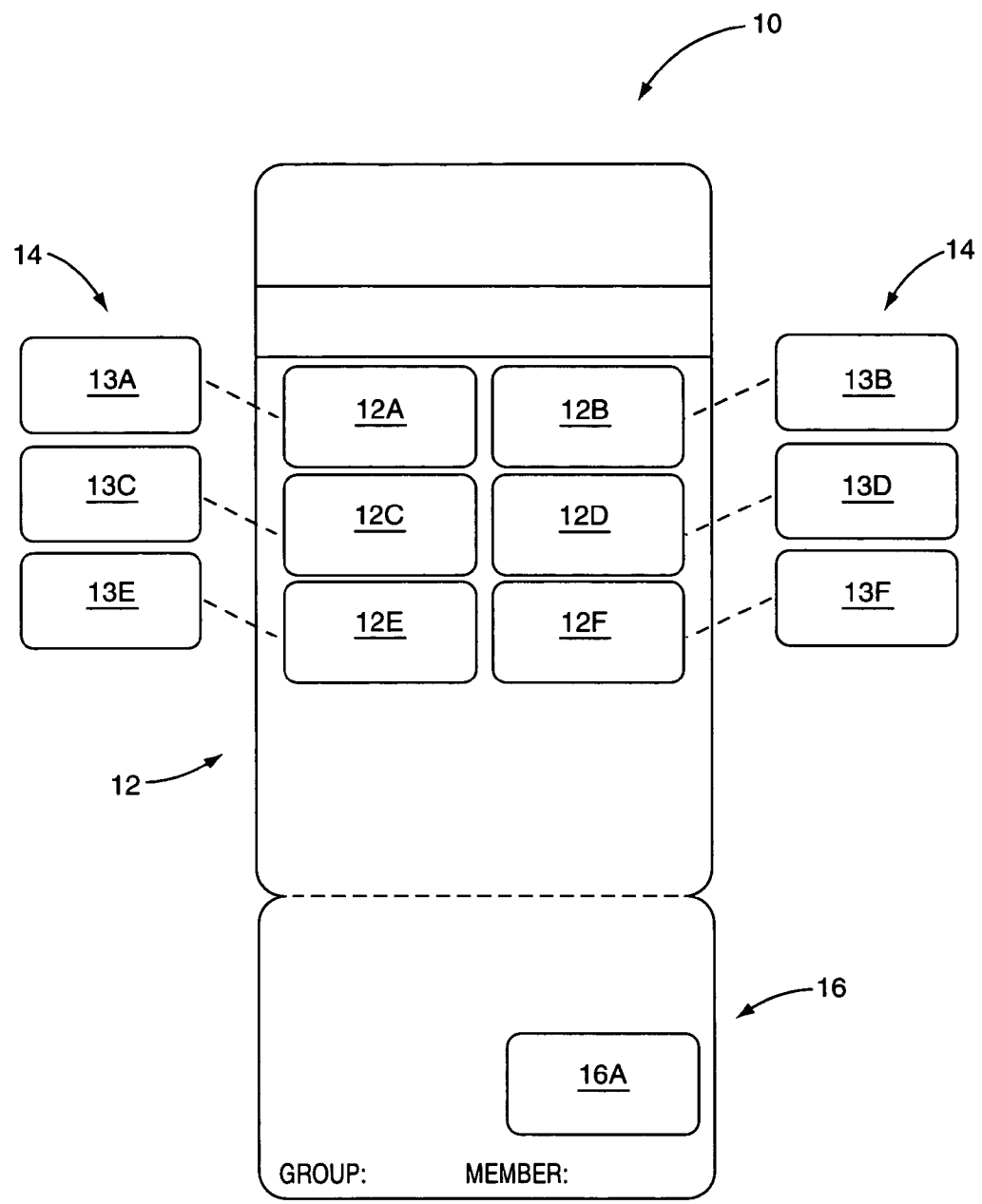
FIG. 1 is a view illustrating the prescription pharmaceutical product promotional carrier of the present invention.

With further reference to the drawings, the prescription pharmaceutical product promotional carrier is shown therein and indicated generally by the numeral 10. Carrier 10 can be constructed of various materials such as paper, cardboard, plastic or the like. As seen in the drawings, the promotional carrier 10 comprises two components. First there is a component indicated generally by the numeral 12. This component is designed to identify a series of prescription pharmaceutical products. In addition, by identifying a series of prescription pharmaceutical products, the carrier 10 forms an advertising medium that effectively promotes the identified prescription products that appear on the carrier 10. Accordingly, component 12 of the carrier 10 includes prescription product identifiers. These product identifiers can assume various forms. In one embodiment, component 12 includes a series of spaces 12A, 12B, 12C, 12D, 12E and 12F. The product identifiers 14 can be in the form of a series of stickers 13A, 13B, 13C, 13D, 13E and 13F, with each sticker being applied to one of the spaces 12A, 12B, 12C, 12D, 12E and 12F. On the face of each sticker there is information printed or formed that identifies one particular prescription product.

Carrier 10 includes a second component and this second component comprises a payment vehicle that is indicated generally by the numeral 16. The term payment vehicle means a medium or device such as a card, slip of paper, etc. that has associated therewith a value or benefit that can be used by a patient or consumer to pay for at least a portion of the cost of a prescription pharmaceutical products. The carrier 10 can include one or more separate payment vehicles. In a preferred embodiment, each payment vehicle is separable from the carrier 10 or the first component 12, and the payment vehicle includes a surface 16A for receiving a product identifier such as a sticker 13A, 13B, 13C, 13D, 13E or 13F.

Figure 2:
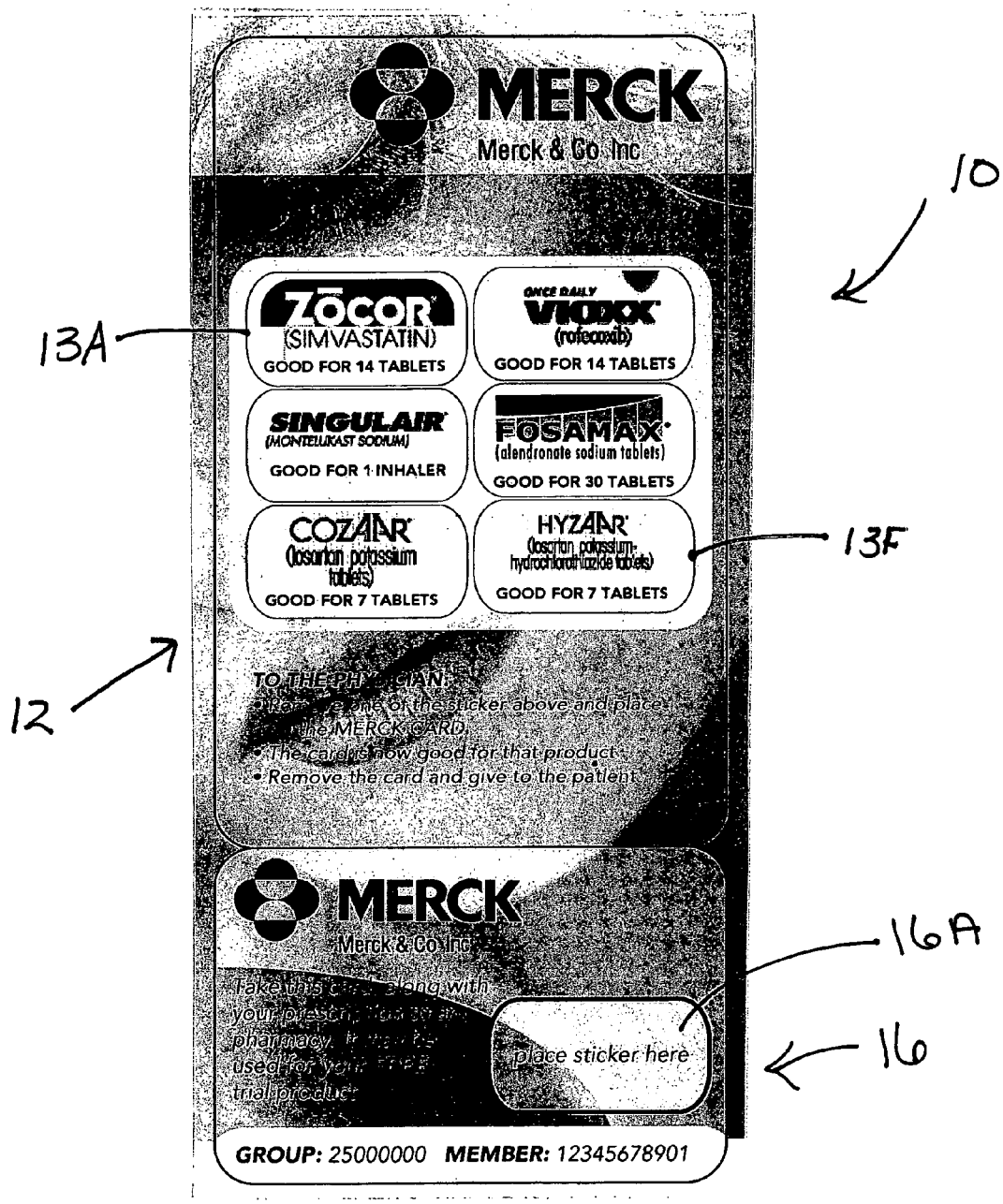
FIG. 2 shows an example of such a promotional carrier.

Each payment vehicle 16 is provided with a unique identifier that will identify that payment vehicle. This unique identifier is stored in a remote database that is managed by an administrator or a pharmacy benefit manager (PBM). There are a number of ways to provide a unique identifier to each payment vehicle of each carrier 10. In one approach, each payment vehicle would be given a member number, for example. Note in the example shown in FIG. 2 where the payment vehicle is given the member number 12345678901. Again, this member number will be stored in the database. In addition, in one preferred approach, each payment vehicle 16 would include a group number. The group number would identify a series of payment vehicles with various member numbers. For example, one group number may encompass a thousand different member numbers. In the example of FIG. 2, note that the group number for the payment vehicle 16 is 25000000. Again the group number would be stored in the database and would be linked to all the payment vehicles having member numbers within that group.

In addition, within one group number there could be subgroups or kits that would also be provided with an identifier. Herein these subgroups will be referred to as kits. A kit, for example, might include twenty promotional carriers 10 all of which would include the same group number, but where each individual payment vehicle would include a unique identifier in the form of a member number. As will be discussed subsequently herein, individual kits can be distributed to doctors and other recipients and because the kits are particularly identified and recorded in the database, the database will accordingly reflect which doctors or recipients issued which payment vehicles.

As discussed above, each of the prescription products promoted on the carrier are identified in a manner that is understandable by both physicians and the ultimate user of the prescription products, the patient or consumer. As shown in the example in FIG. 2, the product identifiers include the brand name of the particular prescription products being promoted by the carrier 10. In addition to the product identification that appears on the face of the carrier 10, the particular prescription products being promoted on the carrier are uniquely identified in the database. The unique identification of each prescription product advertised and promoted on the carrier 10 is linked to a particular payment vehicle or the member number of a payment vehicle. There are numerous ways of accomplishing this. However it is known to identify a prescription product by what is referred to as the National Drug Code, or sometimes referred to as an NDC number. For example, a typical NDC number would include 10 digits such as:

0300-1546-07.

The first four digits of this NDC code identify the manufacturer of the pharmaceutical product. The next four digits identify the particular prescription product. Finally, the last two digits identify the type of packaging for this particular prescription product. Therefore, one way of linking the prescription products being advertised on a carrier 10 with a particular payment vehicle 16 associated with that same carrier 10, would be to store in the database the NDC codes for the prescription products appearing on the carrier and to link each prescription product with the payment vehicle or the member number of the payment vehicle.

Therefore, for each carrier 10, the database would include a unique identifier in the form of a member number for each payment vehicle 16 associated with that carrier. That database would also reflect the group number for each of the payment vehicles. In addition, the database would identify each pharmaceutical prescription product being offered and advertised on the carrier and would link those prescription products on the carrier with the payment vehicle or the payment vehicles associated with that carrier 10. Other information can be placed in the database as well. For example, the kit number for a series of carriers 10 could also be recorded in the database as well as the identity of the physician or recipient of that particular kit. In addition, other information, criteria, process and adjudication instructions can be included in the database and linked to a specific payment vehicle. As will be discussed later, the payment vehicle 16 associated with the carriers 10 will eventually be issued or passed on to patients or consumers that will use the payment vehicles to pay for the cost or a portion of the cost of one or more prescription products being advertised on a carrier 10. Therefore, processing and adjudication information may be incorporated into the database to assist in the processing and adjudication of transactions involving the payment vehicles associated with the various carriers 10.

An example of a prescription pharmaceutical promotional carrier 10 is shown in FIG. 2. Note that the carrier 10 includes six different stickers 13A, 13B, 13C, 13D, 13E and 13F secured to the first component 12 of the carrier. These stickers identify for the patient or consumer six different prescription drugs, Zocor, Vioxx, Singulair, Fosamax, Cozaar, and Hyzaar. Formed about the lower portion of the carrier 10 is the payment vehicle 16. Both the payment vehicle 16 and the upper or first component 12 identify a drug manufacturer. Carrier 10 includes a perforation that extends between the payment vehicle and the first component 12 of the carrier 10. Note also that the payment vehicle 16 in this example includes a space or surface for receiving one of the stickers appearing on the upper portion of the carrier 10.

Figure 3:
FIG. 3 is an example of the payment vehicle separated from the promotional carrier.

After one of the prescription products has been prescribed for a patient by a doctor having the carrier 10, then the doctor simply transfers the appropriate sticker from the upper portion of the carrier to the surface or space provided for on the payment vehicle. See FIG. 3. Before or after a sticker is transferred to the payment vehicle, the payment vehicle is separated from the upper component 12. Eventually, the payment vehicle with the prescription product identifier secured thereto is issued or given to the patient. The patient presents the payment vehicle as shown in FIG. 3 along with the prescription issued by the doctor to the pharmacy.

Figure 4:
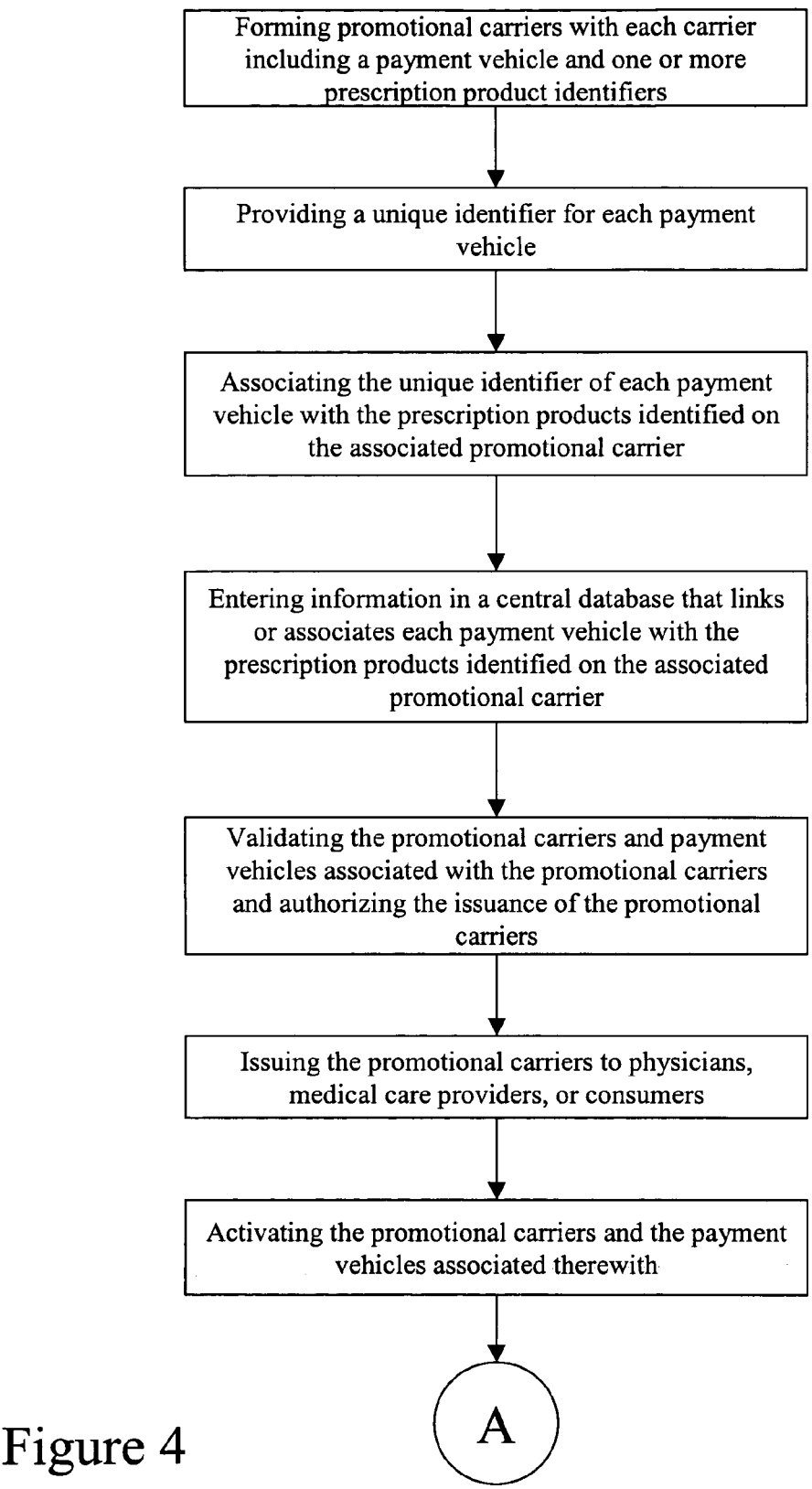
FIGS. 4 and 5 are flow charts illustrating steps involved in implementing an embodiment of the present invention.
Figure 5:
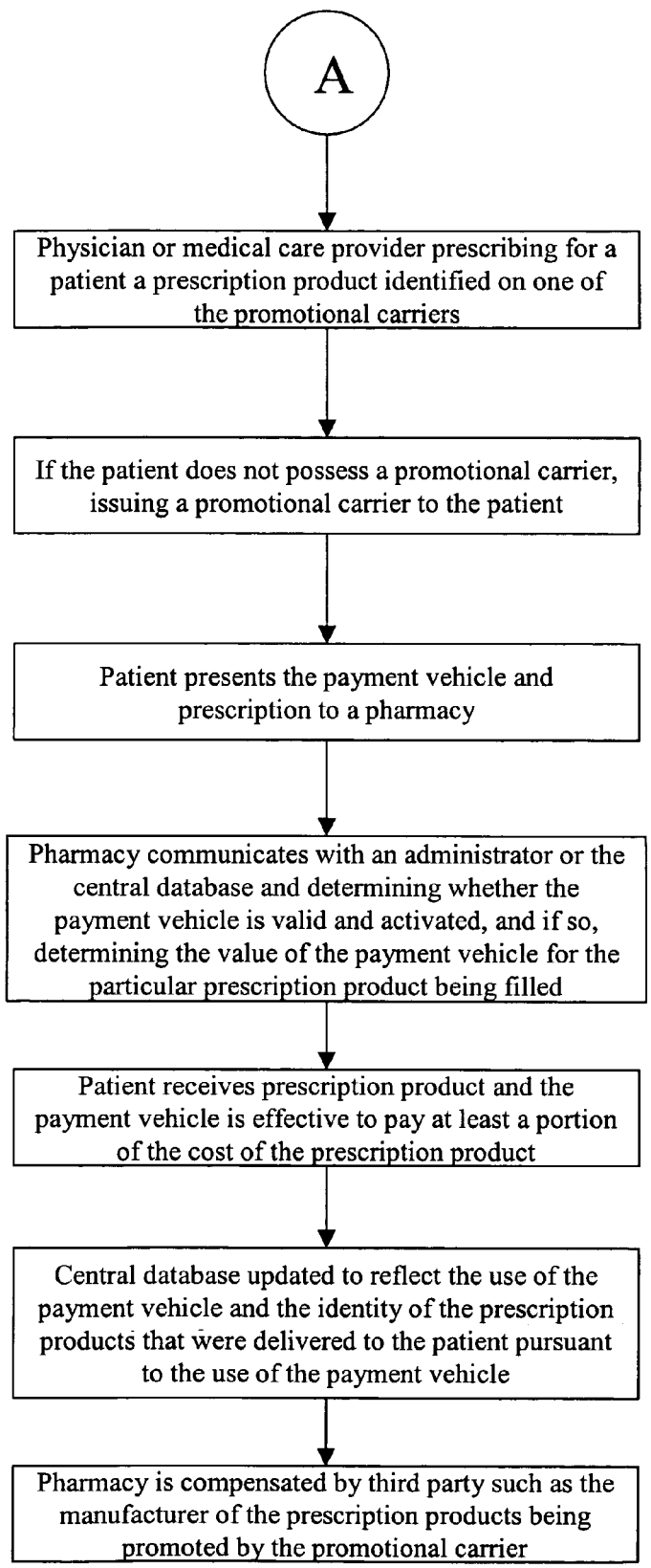

With reference to FIGS. 4 and 5, a flow chart is shown therein and generally describes some of the steps and procedures involved in implementing one embodiment of the present system. As noted therein the carriers 10 are formed and each carrier includes one or more payment vehicles along with a series of prescription product identifiers such as brand names. As discussed above, each payment vehicle includes a unique identifier that is stored in the database and is linked with prescription product identifiers that identify the particular prescription products being promoted on the carrier 10. Once the carriers have been formed, appropriately packaged and the pertinent information and data concerning the carriers has been entered into the database, the carriers 10 are ready to be validated in the database. By validating a group of carriers 10, this means that the respective carriers of the validated group are now ready to be issued to physicians, hospitals, medical care providers, or directly to consumers. In any event, the validation is recorded in the database.

After validation, the carriers 10 can be issued to pharmaceutical sales representatives, for example, and the representatives can in turn distribute the carriers 10 to doctors, hospitals, medical care providers or consumers. In a typical situation, a carrier would promote a series of prescription products manufactured by a single pharmaceutical manufacturer. In this case sales representatives of that manufacturer would distribute the carriers, perhaps in kit form, to doctors who would in turn utilize the carriers and particularly the payment vehicle 16 associated therewith their patients.

The system and method presented herein may require an activation step. Even though the carriers 10 may have been previously validated, the method may require the doctor, the sales representative, the patient or a combination of these individuals to activate a particular carrier or a number of carriers. For example, the method may require the receiving physician to communicate with the administrator or PBM that he or she has received a number of carriers 10 and that the doctor wishes to activate them. Identifying information identifying the payment vehicles associated with the carriers can be communicated to the administrator or PBM and in the process information concerning the doctor can also be entered into the database. This information would, of course, include the doctor's name, location, area of practice, etc. This information collected over time will assist pharmaceutical manufacturers in building a strong relationship with doctors and patients, and will be useful information derived on an ongoing basis concerning the effectiveness of this means of promoting prescription pharmaceutical products.

In the course of examining patients, a doctor may decide to prescribe one of the prescription drugs being promoted on one of the carriers 10 that he or she has received. After writing the prescription for that particular pharmaceutical drug, the doctor can detach one of the payment vehicles 16 from the carrier 10 and place one of the prescription product identifiers (stickers, 13A, 13B, 13C, 13D, 13E or 13F) on the payment vehicle and give to the patient. In a case where the carrier includes stickers that identify the prescription products being promoted, the doctor can simply remove the appropriate sticker from the first component 12 of the carrier 10 and stick the sticker on the surface of the payment vehicle 16 in the area provided for the stickers. Then the patient, with the payment vehicle 16 and a prescription for the prescription product now identified on the payment vehicle, takes the payment vehicle 16 to a pharmacy. The patient presents both the prescription from the doctor and the payment vehicle 16 to the pharmacy. Typically, the payment vehicle will have basic instructions provided on the back thereof describing how the payment vehicle is to be used in processing and adjudicating the benefit carried by the payment vehicle. In typical situations, the pharmacy will contact an appropriate administrator or a PBM that manages the program that the payment vehicle forms a part of. The communication between the pharmacy and the administrator or PBM can be similar to the same type of communications that exist today between pharmacists and PBMs concerning prescription drug cards issued by insurance companies. That is, the communication can be electronic or can be telephonic. In any event, the pharmacy will contact the administrator or PBM and in the process the member number associated with the payment vehicle is communicated. The administrator or PBM will consult the database and determine if this particular payment vehicle has been validated and if an activation step is required, if the payment vehicle has been activated. If, for example, validation and activation are both required and if either one is not present, then a communication is directed to the pharmacy indicating that there are no benefits associated with that particular payment vehicle. If, on the other hand, these preliminary criteria are satisfied, then the process compares the identified prescription product on the payment vehicle with the prescription product identifiers (e.g., NDC codes) in the database that are linked to that particular payment vehicle. Assuming that the database reflects that this particular payment vehicle can be utilized for the prescription product identified on the payment vehicle, then the pharmacy is authorized to fill the prescription and to confer the payment or benefit provided for that particular payment vehicle.

At some point, the database is updated to reflect the use of the payment vehicle. In particular, the database will reflect the identity of the filling pharmacy and the identity of which prescription product was filled in response to the payment vehicle being presented.

It follows that the database can be programmed to control many different factors relating to the utility or use of the one or more payment vehicles associated with a particular carrier 10. That is, for example, the system can be programmed to include on each carrier four separate prescription products and two payment vehicles. In one implementation of the system, each payment vehicle would be valid for use with only one of the identified prescription products appearing on the carrier 10. Thus, when the two payment vehicles carried by the single carrier have been presented and effectively used, then the database would reflect that the carrier and its associated payment vehicles were no longer valid for any use. Alternatively, and again in the way of an example only, the carrier may promote four different prescription products and provide only a single payment vehicle but where the database may be programmed to enable one of the prescription products to be revealed a number of times. It will be appreciated, that other variations and limitations can be programmed into the database. Again, in the way of an example, the particular number of tablets dispensed pursuant to this program can be varied and many other limitations and extensions can be programmed.

Upon fulfillment of the prescription by the pharmacy, the database indicates the utilization of the payment vehicle and the benefit conferred by the payment vehicle. Thereafter the administrator or PBM will reimburse the pharmacy for the benefit conferred and possibly and additional fee to cover administrative costs. Ultimately the benefit conferred is paid by the sponsorer of the carrier 10 having the particular payment vehicle 16 associated therewith. Generally this would be the manufacturer, or a party acting on behalf of the manufacturer, whose prescription product was promoted by the carrier and filled pursuant to the method described above. Processing and adjudicating the benefit associated with the payment vehicle are generally no different from those employed by PBMs and other administrators that administer insurance sponsored drug prescription cards.

One of the many advantages of the present invention is that it presents a method of promoting and advertising prescription pharmaceutical products in a controlled environment where the prescription product samples dispensed can be accurately tracked and controlled. Further, the system and method of the present invention has the ability to extract and record a wealth of information that can be provided to the manufacturer of the prescription products being promoted on the carriers 10. This information can be used to plan and adjust marketing and advertising programs. In addition the system and method described above enables pharmaceutical manufacturers to advertise and promote a number of prescription products on a single advertising piece and yet limit its liability with respect to costs for sample prescription products.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

The invention claimed is:

1. A method of promoting one or more prescription pharmaceutical products comprising:
   a. securing one or more transferable stickers to a carrier where each sticker identifies at least one prescription pharmaceutical product;
   b. providing a payment vehicle for paying at least a portion of the cost of one of the prescription pharmaceutical products identified by the stickers and wherein the payment vehicle forms a part of the carrier;
   c. electronically associating in a database all of the prescription pharmaceutical products identified by the stickers with a number on the payment vehicle, wherein the database is associated with a central computing station;
   d. after the payment vehicle is presented to the pharmacy, receiving electronically communicated information at the database indicating the number associated with the payment vehicle and the prescription pharmaceutical product identified by one of the stickers that has been transferred onto the payment vehicle;
   e. comparing the number electronically received at the database with the prescription pharmaceutical product identified by the sticker on the payment vehicle;
   f. electronically communicating to the pharmacy through the central computing station that the payment vehicle is valid and can be used to pay for at least a portion of the cost of the prescription pharmaceutical product identified by the sticker transferred onto the payment vehicle.

2. The method of promoting prescription pharmaceutical products of claim 1 including updating the database indicating the use of the payment vehicle and identifying the sticker or stickers carried by the payment vehicle or the prescription pharmaceutical product identified thereby such that the database reflects information that identifies which prescription pharmaceutical product or products were filled pursuant to the payment vehicle presented to the pharmacy.

3. A method of promoting one or more prescription pharmaceutical products, comprising:
   d. identifying one or more prescription pharmaceutical products on a promotional carrier;
   e. providing at least one payment vehicle that forms a part of the carrier;
   f. uniquely identifying the payment vehicle with a payment vehicle identifier and electronically storing the identifier in a remote database associated with a central computing station;
   d. for each carrier, electronically linking in the database the payment vehicle identifier with the identified prescription products of the carrier such that the database reflects which prescription products are associated with each payment vehicle;
   e. receiving electronically communicated information at the database through the central computing station indicating that a pharmacy has received one of the payment vehicles and identifying the payment vehicle identifier associated with the payment vehicle and one of the identified prescription products;
   f. comparing the payment vehicle identifier to the identified prescription product in the database;
   g. wherein the payment vehicle is used to pay for at least a portion of the cost of the identified prescription product.

4. The method of claim 3 wherein the carrier includes product identifiers that identify the prescription products being promoted by the carrier and wherein the product identifiers assume a space on the carrier separate from the payment vehicle and wherein the product identifiers are transferable to the payment vehicle.

5. The method of claim 4 wherein the product identifiers include a series of stickers with each sticker having a face that includes the identity of at least one prescription pharmaceutical product.

6. The method of claim 5 including distributing the promotional carrier to a physician or other medical care provider.

7. The method of claim 3 wherein the payment vehicle is presented to a pharmacy and the pharmacy communicates with the database or with an administrator that has access to the database such that after the payment vehicle is utilized the database is updated to reflect the use.

8. The method of claim 6 further comprising receiving a request to activate the promotional carrier after the promotional carrier is distributed to the physician or other medical care provider.

9. The method of claim 8 further comprising comparing at least one of the product identifiers with the payment vehicle identifier in the database.

10. The method of claim 9 wherein after at least one of the product identifiers is compared to the payment vehicle identifier, the method includes authorizing a pharmacy to confer a benefit provided by the payment vehicle.

11. The method of claim 9 wherein after the pharmacy confers the benefit provided by the payment vehicle, the method includes updating the database to indicate that the benefit conferred by the payment vehicle has been received and the payment vehicle is no longer valid.

12. The method of claim 1 further comprising distributing the promotional carrier to physician or other medical care provider and comprising receiving a request to activate the carrier after the promotional carrier is distributed to the physician or other medical care provider.

13. The method of claim 12 wherein the stickers each include a product identifier and the payment vehicle includes a payment vehicle identifier and the method includes comparing at least one product identifier with the payment vehicle identifier in the database.

14. The method of claim 13 wherein after the product identifier is compared to the payment vehicle identifier, the method includes authorizing a pharmacy to confer a benefit provided by the payment vehicle.

15. The method of claim 14 wherein after the pharmacy confers the benefit provided by the payment vehicle, the method includes updating the database to indicate that the benefit conferred by the payment vehicle has been received and the payment vehicle is no longer valid.

* * * * *